United States Patent
Sun et al.

(10) Patent No.: US 10,011,848 B2
(45) Date of Patent: Jul. 3, 2018

(54) SYSTEM AND METHOD FOR DELIVERY OF SUBSTANCE INTO MAMMALIAN CELLS

(71) Applicant: CITY UNIVERSITY OF HONG KONG, Kowloon Tong (HK)

(72) Inventors: Dong Sun, Hong Kong (CN); Yu Ting Chow, Hong Kong (CN); Ran Wang, Hong Kong (CN)

(73) Assignee: CITY UNIVERSITY OF HONG KONG, Kowloon Tong (HK)

(*) Notice: Subject to any disclaimer, the term of this patent is extended or adjusted under 35 U.S.C. 154(b) by 0 days.

(21) Appl. No.: 15/346,777

(22) Filed: Nov. 9, 2016

(65) Prior Publication Data

US 2018/0127782 A1   May 10, 2018

(51) Int. Cl.
  *C12N 15/87* (2006.01)
  *B22F 1/00* (2006.01)
  *B82Y 25/00* (2011.01)

(52) U.S. Cl.
  CPC .................... *C12N 15/87* (2013.01)

(58) Field of Classification Search
  CPC .................................................. C12N 15/87
  USPC .......................................... 435/283.1
  See application file for complete search history.

(56) References Cited

U.S. PATENT DOCUMENTS

| | | |
|---|---|---|
| 5,459,127 A | 10/1995 | Felgner et al. |
| 5,643,599 A | 7/1997 | Lee et al. |
| 5,804,604 A | 9/1998 | Frankel et al. |
| 5,925,628 A | 7/1999 | Lee et al. |
| 7,420,031 B2 | 9/2008 | Karas |
| 8,063,131 B2 | 11/2011 | Gao |
| 8,865,216 B2 | 10/2014 | Labhasetwar et al. |
| 8,957,186 B2 | 2/2015 | Ahn et al. |
| 2006/0083711 A1 | 4/2006 | Berry et al. |

(Continued)

FOREIGN PATENT DOCUMENTS

| | | |
|---|---|---|
| WO | 91/17424 | 11/1991 |
| WO | 2013/059343 A1 | 4/2013 |

OTHER PUBLICATIONS

Silva et al., Gold coated magnetic nanoparticles: from preparation to surface modification for analytical and biomedical applications, May 10, 2016, Chem. Commun., 52 (Year: 2016).*

(Continued)

*Primary Examiner* — Kevin Joyner
*Assistant Examiner* — Holly M Mull
(74) *Attorney, Agent, or Firm* — Melvin Li; Heslin Rothenberg Farley & Mesiti PC

(57) ABSTRACT

The present invention is concerned with a system of delivering particles of nano-scale into mammalian cells with a diameter of 50 μm or less. The system has a container containing the mammalian cells, the particles, a pressure-exerting member for generating transient apertures of substantially 1-200 nm on surface of the cells, a magnetic mechanism configured to generate a magnetic force to act on the pressure-exerting member thus to move the pressure exerting member, a control mechanism for effecting movement of the pressure-exerting member in a predetermined motion pattern, a measuring mechanism configured to indicate magnitude of pressure exerted on surface of the mammalian cells, and a monitoring mechanism.

9 Claims, 12 Drawing Sheets

(56) References Cited

U.S. PATENT DOCUMENTS

| | | | | |
|---|---|---|---|---|
| 2011/0262891 A1* | 10/2011 | Ozaki | ............... | C12M 35/02 |
| | | | | 435/3 |
| 2012/0234109 A1* | 9/2012 | Sears | ............. | G01R 33/0385 |
| | | | | 73/862.381 |
| 2014/0273229 A1 | 9/2014 | Meacham et al. | | |
| 2015/0219640 A1* | 8/2015 | Lim | ............. | G01N 33/54313 |
| | | | | 435/5 |
| 2016/0089447 A1 | 3/2016 | Divita et al. | | |
| 2017/0175102 A1* | 6/2017 | Chiou | ............... | C12N 13/00 |

OTHER PUBLICATIONS

Derossi, et al., Trojan peptides: the penetratin system for intracellular delivery, Cell Biology, vol. 8, Feb. 1998.

Gupta, et al., Intracellular delivery of large molecules and small particles by cell-penetrating proteins and peptides, Advanced Drug Delivery Review, Elsevier, pp. 637-651, 2005.

Hogg, et al., An automated system for intracellular and intranuclear injection, Journal of Neuroscience Methods, Elsevier, vol. 169, pp. 65-75, 2008.

Kolhar, et al., Polymer Nanoneedle-Mediated Intracellular Drug Delivery, Wiley-VCH Verlag GmbH & Co., No. 14, pp. 2094-2100, 2011.

Wong, et al., Functionalization of Carbon Nanotubes via Cleavable Disulfide Bonds for Efficient Intracellular Delivery of sIRNA and Potent Gene Silencing, JACS Communications, vol. 127, pp. 12492-12493, 2005.

\* cited by examiner

SYSTEM AND METHOD FOR DELIVERY OF SUBSTANCE INTO MAMMALIAN CELLS

FIELD OF THE INVENTION

The present invention is concerned with a system and a method for delivery of substance into living cell and in particular mammalian cells.

BACKGROUND OF THE INVENTION

There are various conventional methodologies of introducing substances into living cells. One such methodology is concerned with the use of a vehicle, such as carbon nanotubes, to deliver a desired substance. However, the fabrication of carbon nanotubes with precise desired characteristics needed is not reliable and the fabrication cost is very high. Another methodology is concerned with the use of peptides as a vehicle. Whether the delivery of the substance is achieved by way of nano-carbons or peptides, the substance would need to firstly bind with the delivery vehicle. The binding would, or at least could, affect the properties of the substance and cause undesirable side effects. The delivered substance may not achieve what it is intended to achieve in the cells after delivery.

There have also been proposals to use nano-needles to deliver substances. The use of such needles effectively create apertures on the cell surface by mechanically poking the cell membrane. This process is often rather difficult to control and would cause a significantly percentage of cell death.

The present invention seeks to address these issues, or at least to provide an alternative to the public.

SUMMARY OF THE INVENTION

According to a first aspect of the present invention, there is provided a system of delivering particles of nano-scale into mammalian cells with a diameter of 50 µm or less, comprising a container containing the mammalian cells, the particles, a pressure-exerting member for generating transient apertures of substantially 1-200 nm on surface of the cells, a magnetic mechanism configured to generate a magnetic force to act on the pressure-exerting member thus to move the pressure exerting member, a control mechanism for effecting movement of the pressure-exerting member in a predetermined motion pattern, a measuring mechanism configured to indicate magnitude of pressure exerted on surface of the mammalian cells, and a monitoring mechanism, wherein:
  the pressure-exerting member has a length not longer than one-third of the width of the container;
  the pressure exerting member and the particles are free of chemical bonding before a delivery exercise; and
  the system is free of use of electrical field in the delivery of the particles.

Preferably, the container may be in the form of a Petri dish, and the pressure-exerting member has a cylindrical profile, with an outer shell containing an iron core and a biocompatible material for securing the iron core in the outer shell.

In an embodiment, the outer shell may be made of an inert material or glass, and the biocompatible material may be polydimethylsiloxane.

In one embodiment, the container or the Petri dish may have a diameter of substantially 35 mm, the pressure-exerting member may have a length of substantially 1 cm and inner and outer diameters of substantially 0.7 mm and 1 mm, respectively, and the iron core may have a length of substantially 0.75 cm. The outer shell may be open-ended to expose the iron core.

Preferably, the system may comprise a first stage for supporting the container, the first stage may be configured to be movable vertically and linearly for adjusting the position of the container. The magnetic mechanism may include i) a magnet situated below the first stage and ii) a second stage supporting the magnet, the second stage is configured to be movable linearly, whereby movable of the second stage produces corresponding movement of the magnet. The monitoring mechanism may include a camera situated above the first stage for monitoring movement of the pressure exerting member in use. The system may comprise a balance on which the second stage situates, the balance for detecting and indicating magnetic force generated on the pressure exerting member in the container. The system may comprise a computer system for coordinating movement of the magnet and thus the magnetic force generated on the pressure exerting member, controlling horizontal position of the second stage, controlling horizontal position and vertical position of the first stage, and movement of the pressure exerting member in the container during a particle delivering exercise.

BRIEF DESCRIPTION OF THE DRAWINGS

Some embodiments of the present invention will now be explained, with reference to the accompanied drawings, in which.

DETAILED DESCRIPTION OF PREFERRED EMBODIMENTS OF THE INVENTION

This invention is concerned with systems, an apparatuses and methods for use in conducting high-throughput intracellular delivery of substance into biological cells. In one embodiment, this invention makes use of a robotic device and a pressure exerting member to deliver extracellular substance into biological cells residing in a container such as a Petri dish. The use of a robotic device can effect the delivery in a faster and reproducible manner. A 3-DOF (three degree of freedom) microrobotic system equipped with a magnet is involved to conduct the intracellular delivery task. The pressure exerting member, e.g. a magnetic glass rod, is used to apply force onto the cell surface. To transfer materials into cells, the magnetic glass rod exerts compression and shear force on the cell surface. The magnetic glass rod is caused to move by external magnetic field generated by the magnet. The applied force on the magnetic glass rod can be controlled by adjusting the distance between the magnetic glass rod and the magnet. Studies leading to the present invention demonstrates that the magnetic glass rod is capable to deliver various macromolecules into cell with high efficiency. This methodology has been demonstrated to be able to efficiently deliver plasmid DNA or tetramethylrhodamine isothiocyanate-dextran into living cells and in particular mammalian cells. Fabrication of such a pressure exerting member, e.g. magnetic glass rod, requires a glass capillary, an iron core (e.g. in the form of a rod), and polydimethylsiloxane. The following illustrates different aspects of the present invention in greater detail.

Figure 1:
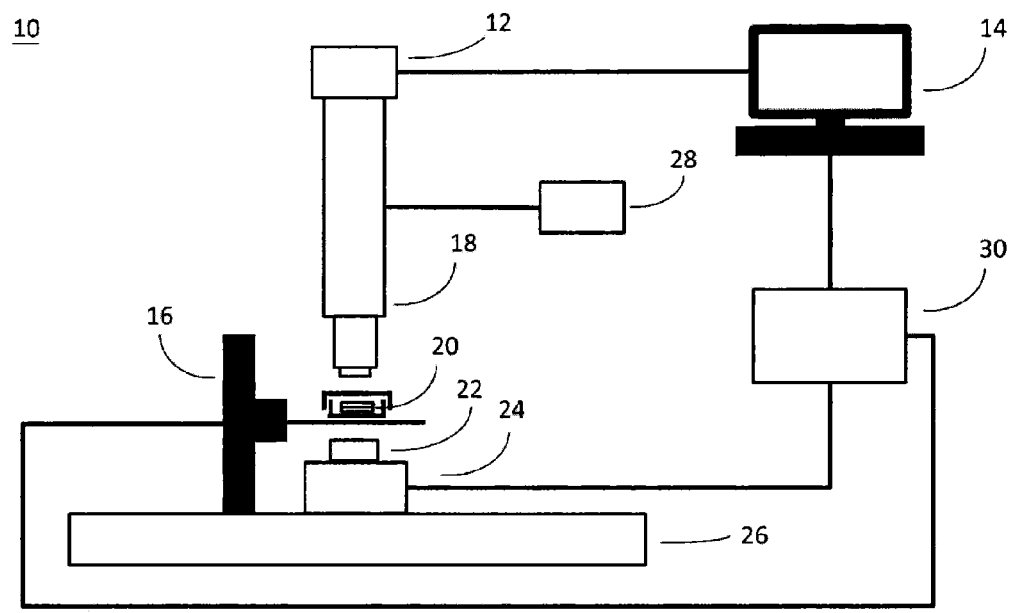
FIG. 1 is a schematic diagram showing an embodiment of an intracellular delivery system in accordance with the present invention.

FIG. 1 is a schematic diagram showing an embodiment of an intracellular delivery system 10 in accordance with the present invention. In this embodiment, the intracellular delivery system 10 is conducted via a microrobotic system including a motorized stage 24 movable in an X-Y plane (XY stage) and a motorized stage 16 movable in a Z plane (Z-stage). A pressure exerting member 20, such as a magnetic glass rod 20, is placed in a container such as a cell culturing Petri dish on the Z-stage 16. A magnet 22 is placed on another container on the X-Y stage 24, the magnet 22 providing a magnetic force and acting on magnetic glass rod 20 for effecting movable and thus cause compression and stretching of cells in the Petri dish on the Z-stage. The magnetic force from the magnet 22 on the magnetic glass rod 20 is adjustable by changing the distance between the magnet 22 and the magnetic glass rod 20. This is achieved by moving the Z-stage vertically to a desired vertical position. In this embodiment, the magnetic glass rod 20 has an outer diameter of 1 mm and a length of 1 cm. The magnetic glass rod includes an iron core, e.g. an iron rod, fixed within a glass tube or capillary. The glass tube is then filled with an inert or biocompatible substance such as poly(dimethylsiloxane) PDMS. The intracellular delivery system also includes an imaging (or vision) system. An image detector 12, such as a CCD camera, is mounted on a microscope 18, which is situated above the magnetic glass rod 20. A light source 28 is provided to illuminate for assisting the wording of the microscope 18. A control system 14, which may be a personal computer, can control the positions of the X-Y stage 24 and the Z stage 16 through a motion controller 30. In addition, arbitrary patterns can be inputted into the control system 14 for drawing patterns automatically. For example, a preferred movable pattern may be such that the path of the magnetic glass rod would cover and swipe the entire bottom surface of the container a predetermined number of times. Preferably, the intracellular delivery system 10 is installed on an anti-vibration table 26.

Figure 2:
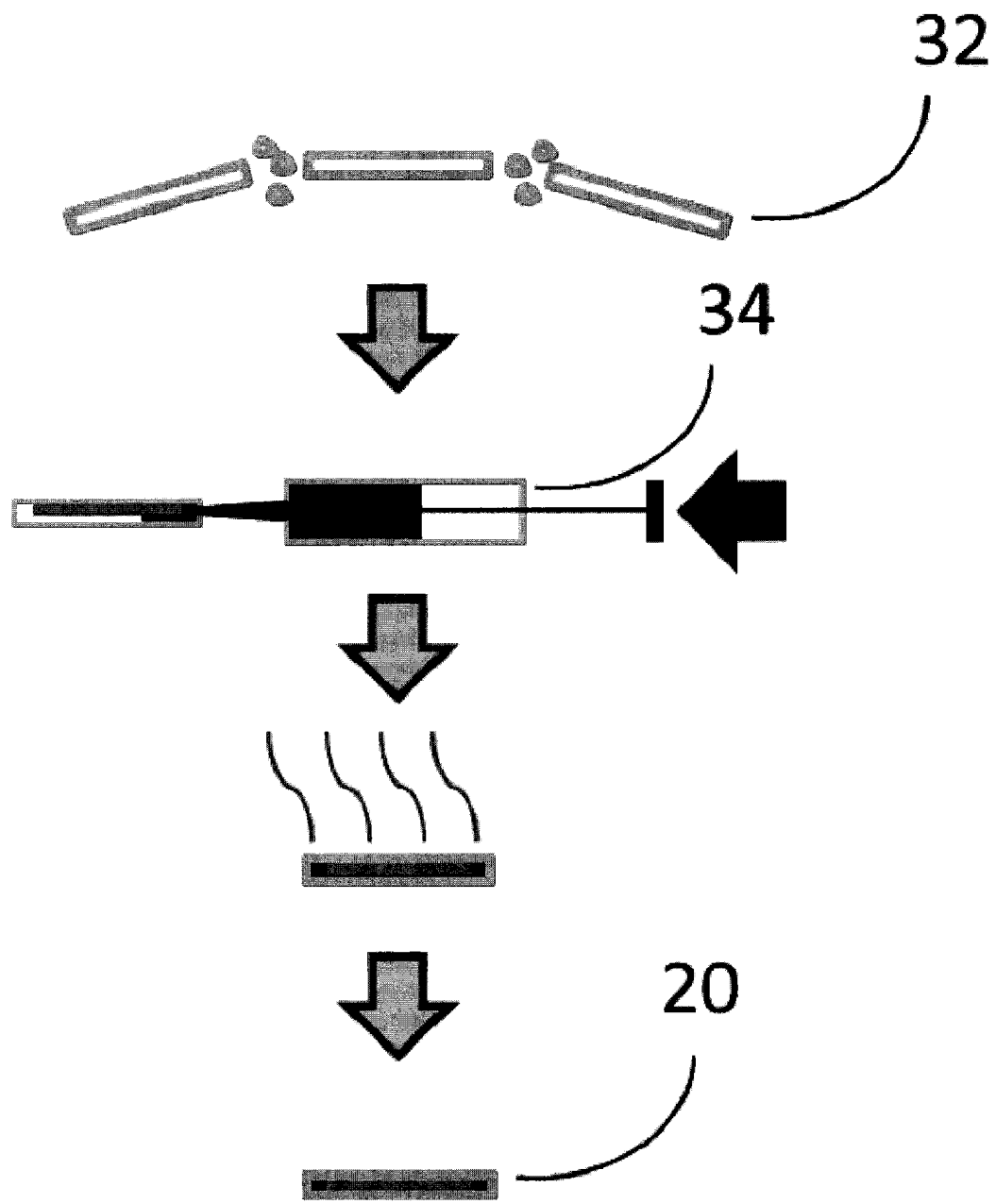
FIG. 2 is a schematic diagram showing an embodiment a pressure exerting member comprised in the intracellular delivery system.

FIG. 2 illustrates how the pressure exerting member 20 may be fabricated. In this embodiment, the magnetic glass rod 20 typically includes a thin-walled borosilicate tubing with a diameter of 1 cm that has been cut into 1-cm-long pieces. A staple trimmed and sized into 1-cm-long pieces is then inserted into the glass tubing 32. PDMS is mixed with a curing agent in a 1:10 (w/w) ratio and injected into the glass tubing via a 1 mL syringe 34. The glass tubing is subsequently baked in an oven at 75° C. for 1.5 h. Finally, a magnetic glass rod 20 is fabricated.

Figure 3A:
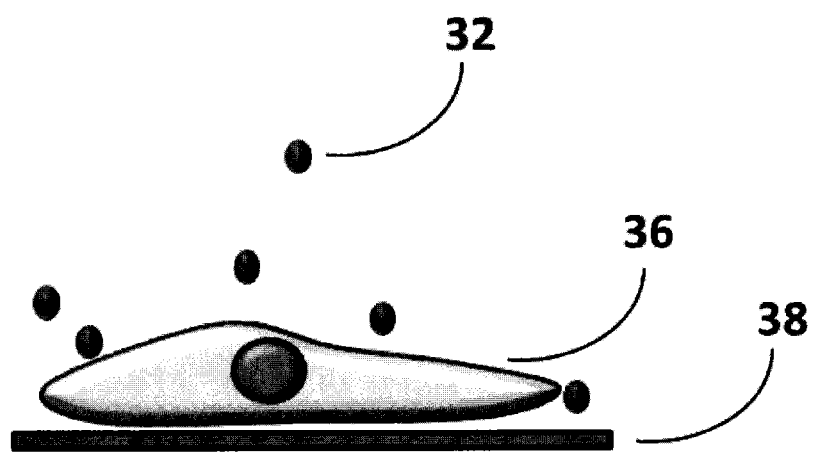
FIGS. 3A-3D are a series of schematic diagram showing steps of delivery of substance into cells in accordance with the present invention.
Figure 3B:
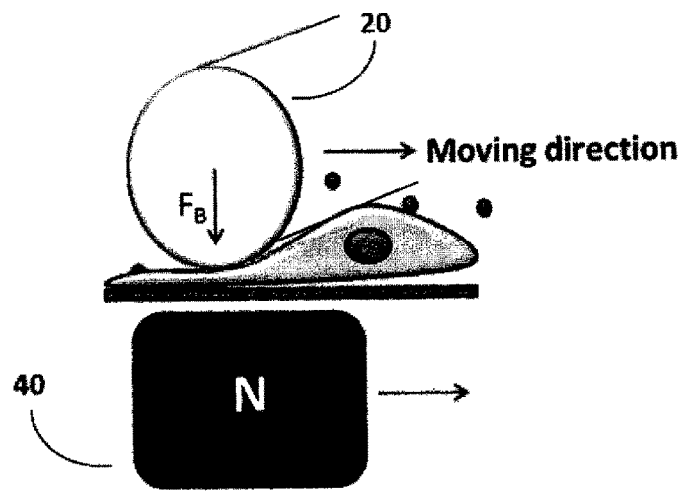
Figure 3C:
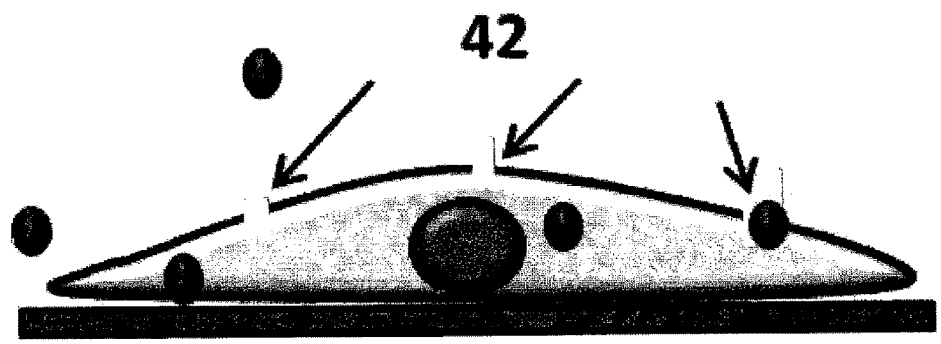
Figure 3D:
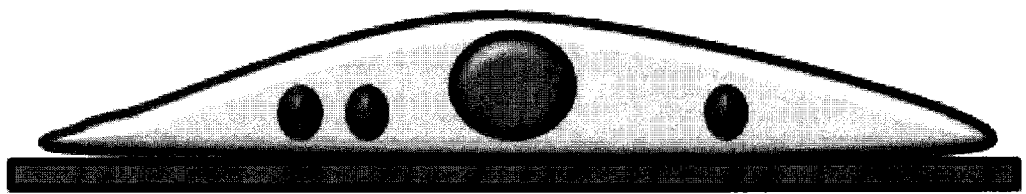
Figure 4:
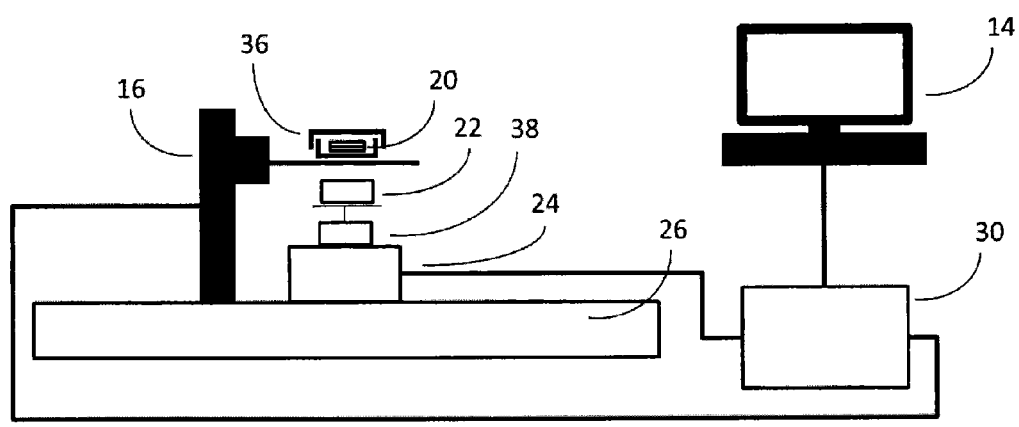
FIG. 4 is a schematic diagram showing a step adopted for force calibration of the system of FIG. 1 prior to delivery of the substance shown in FIGS. 3A-3D.

The working principle of the magnetic force-induced intracellular delivery system is illustrated in FIGS. 3A-3D. First, the to-be-delivered substance or particles 32 is added into the dish (FIG. 3A). The magnetic glass rod 20 is subsequently placed in the dish 38, and a magnet 22 is placed at the bottom of the dish 38. The magnet 22 is moved slowly to guide the movement of the magnetic glass rod 22. The cell 36 experiences the compression and stretching forces exerted by the magnetic glass rod 22 (FIG. 3B), which creates transient holes 32 on the cell membrane. The particles 32 in the dish then diffuse into the cells 36 through the transient holes 42 (FIG. 3C). Studies leading to the present invention indicates that a magnetic force as little as 1 mN measured by the balance can generate such transient apertures. However, a more optimal magnetic force is substantially 13 mN for substantially 3 minutes is preferred. The cell membrane returns to normal condition within a few minutes (FIG. 3D).

Figure 5A:
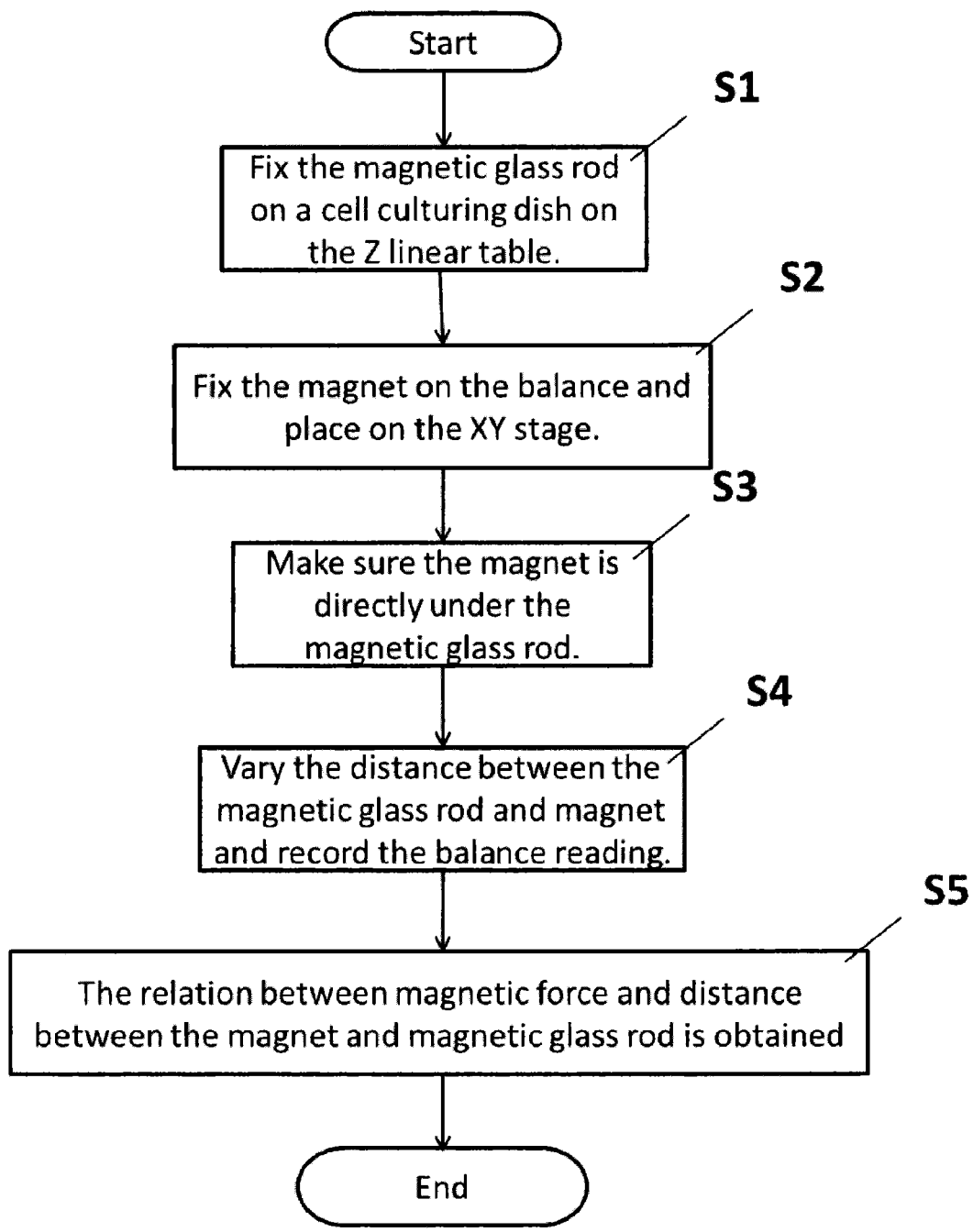
FIG. 5A illustrates in greater detail the force calibration of the system shown in FIG. 4.

FIG. 5A is a flowchart showing a calibration procedure for the embodiment of the present invention. The magnetic glass rod 20 is placed on a cell culturing dish 36, which is subsequently mounted on a Z-stage (horizontal or linear) 16 (S1). A magnet 22 is fixed on a balance. The balance 38 and the magnet 22 are placed on the X-Y stage 24 (S2). The position of the balance 38 is adjusted such that the magnet 22 is directly above the magnetic glass rod 20 (S3). The distance between the magnetic glass rod 20 and the magnet 22 is subsequently changed while the reading on the balance 38 is being recorded (S4). The magnet 22 is indicated to be lighter when it is situated closer to the magnetic glass rod 20 due to the magnetic attractive force between the magnetic glass rod 20 and the magnet. Finally, the relationship between the magnetic force applied on the magnetic glass rod 20 by the magnet 22 and the distance between them is obtained (S5).

Figure 5B:
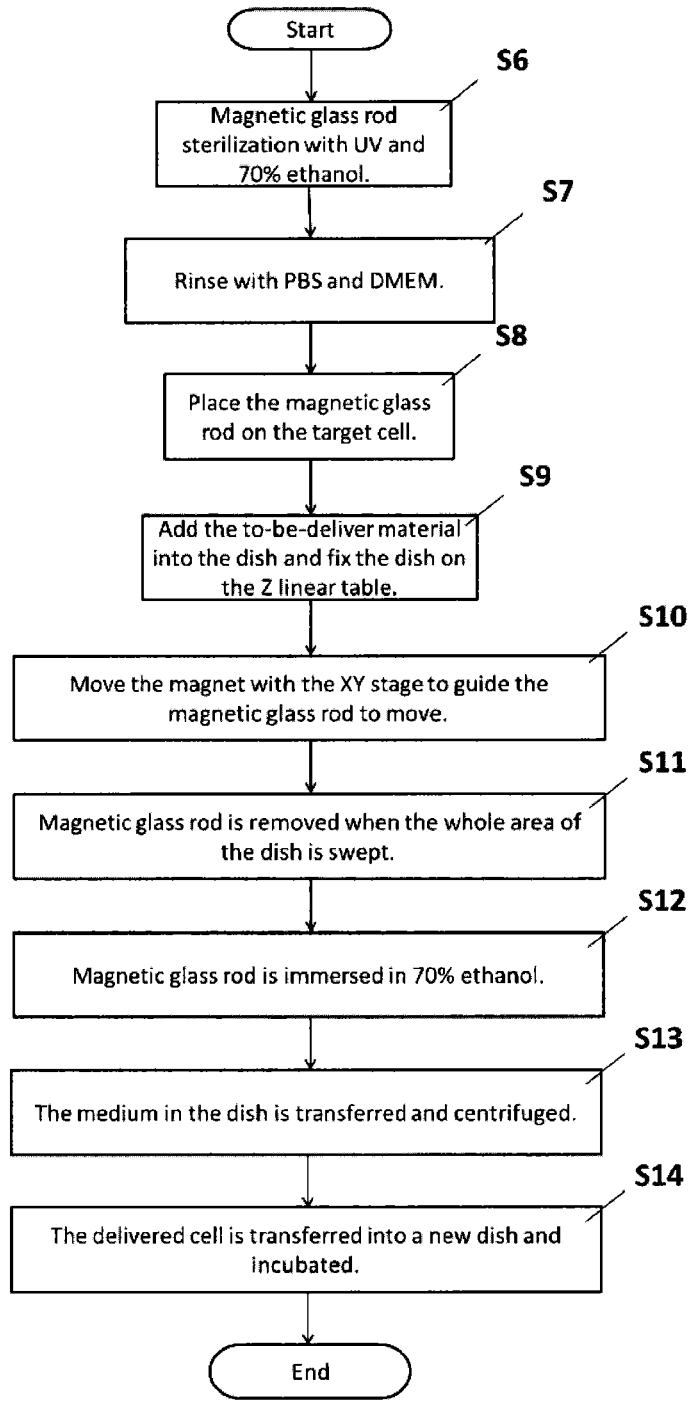
FIG. 5B illustrates in greater detail the intracellular delivery shown in FIGS. 3A-3D.

FIG. 5B illustrates the steps in the intracellular delivery procedure. The magnetic glass rod 20 is sterilized under UV for 30 min and then immersed in 70% ethanol for 5 min (S6). The magnetic glass rod 20 is rinsed with phosphate-buffered saline (PBS) and Dulbecco's Modified Eagle Medium (DMEM) (S7), and then placed on the cell culturing dish 36 containing the target cells (S8). The material to be transfected was added into the cell culturing dish 36, and the calibrated magnet 22 was placed under the cell culturing dish 36 (S9). The magnet 22 slowly moves around the cell culturing dish 36 such that the magnetic glass rod 20 generally follows the motion of the magnet 22 (S10). When the magnetic glass rod 20 sweeps the whole area of the cell culturing dish 36, the magnetic glass rod 20 is then removed (S11) and immersed in 70% ethanol (S12). The medium in the cell culturing dish 36 is then transferred into a 1.5 mL centrifuge tube and spun with 300 g force (S13). The supernatant was removed, and fresh medium was added. The transfected cells are finally transferred into a new cell culturing dish 36 and then incubated (S14).

The following depicts examples conducted with respect to different aspects of the present invention.

EXAMPLES

Figure 6A:
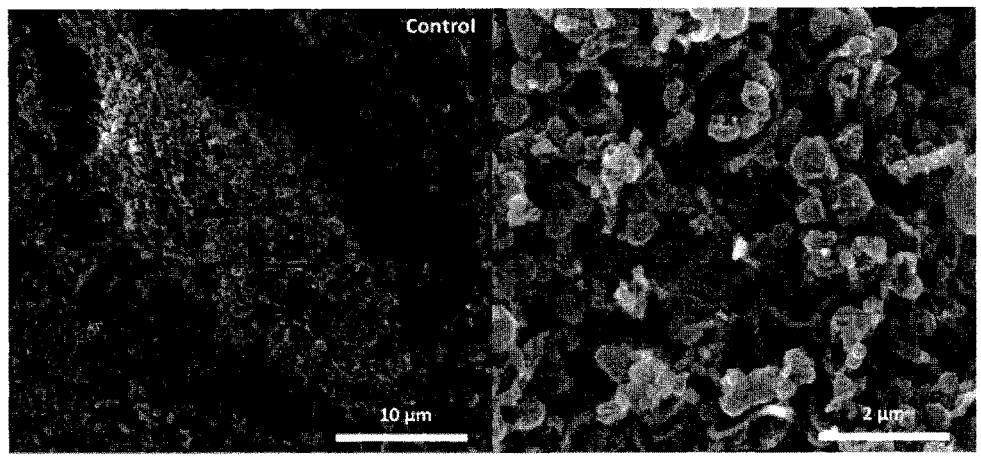
FIGS. 6A-6C are photographic images taken using scanning electron micrograph of a HepG2 cell before and after substance delivery.
Figure 6B:
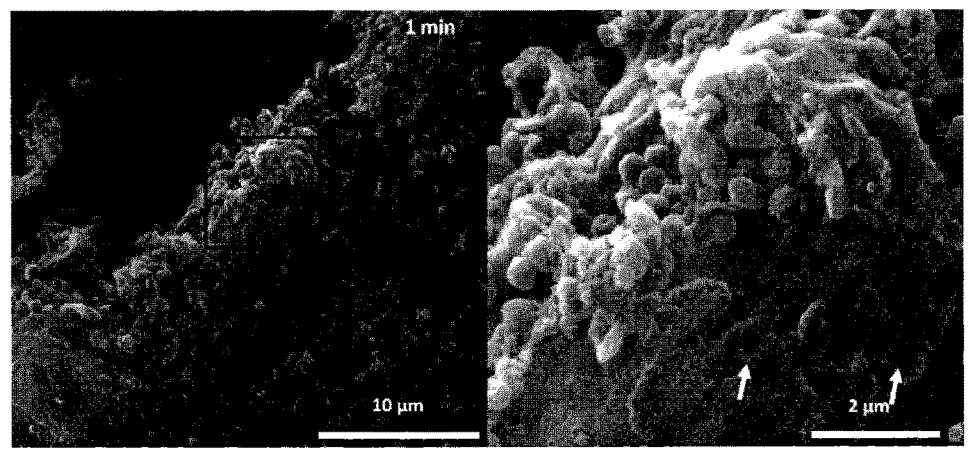
Figure 6C:
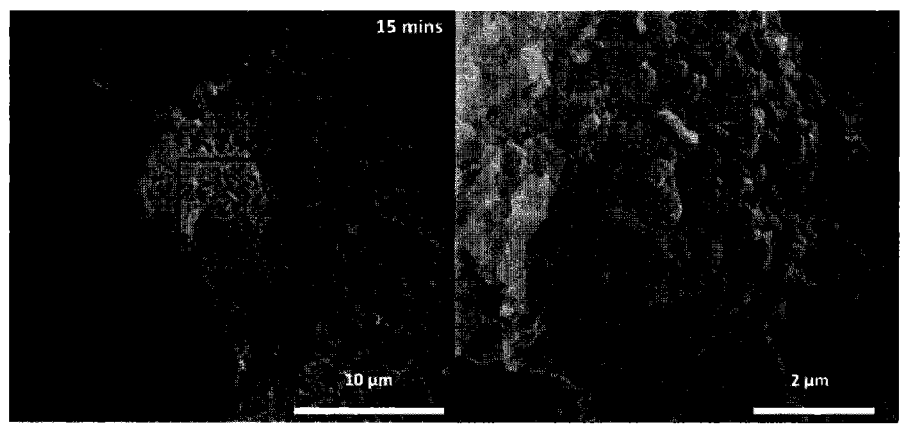

With a view to confirm that that transient holes are generated on the surface of the cells, the morphology of the experimental or processed cells is studied at different times during the manipulation throughout the experiments. FIGS. 6A-6C illustrate that the morphology of the processed cell after 1 min obviously changed. FIG. 6A shows the morphology of untreated cells while FIG. 6B shows the morphology of the processed cells. The change in morphology is more significant, evident and obvious. Please see FIG. 6C. FIG. 6C is an image showing the morphology of a surface of treated cells after a 15-min treatment. The white arrows in, for example, FIG. 6B, indicate the location of the transient holes generated.

Figure 7A:
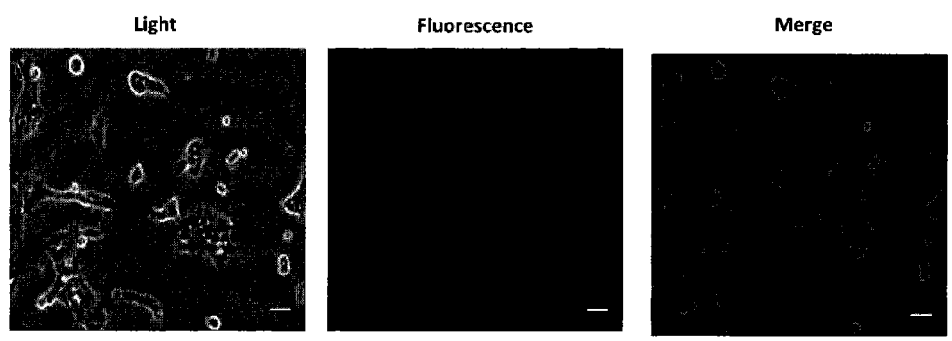
FIGS. 7A-7B are photographic images of HepG2 administrated with TRITC-Dextran and FITC-BSA.
Figure 7B:
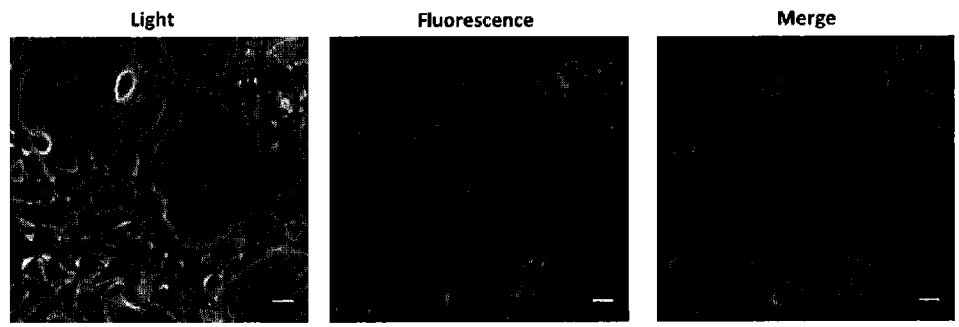
Figure 8A:
FIGS. 8A-8B are photographic images of HepG2 administrated with mChery and GFP plasmid.
Figure 8B:
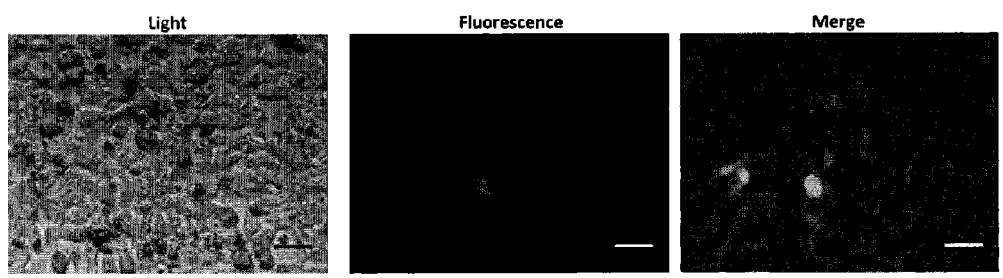
Figure 9:
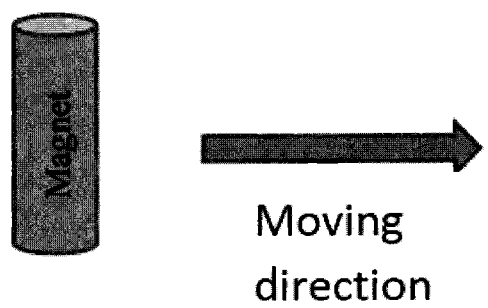
FIG. 9 is a schematic diagram showing a magnet used for exerting a magnetic force to a pressure exerting member for generating transient apertures on cell surface.

FIGS. 7A-7B show the results of 293FT cells delivered with tetramethyl-rhodamine isothiocyanate-dextran (TRITC-dextran) and fluorescein isothiocyanate conjugated with bovine serum albumin (FITC-BSA) by the magnetic glass rod. Spherically, FIG. 7A illustrates that TRITC-dextran was delivered with high efficiency into the cells. The cells loaded with TRITC-dextran remained viable 24 h after the intracellular delivery. The scale bar represents 40 µm. In the second experiment, we used the magnetic glass rod to deliver FITC-BSA into the cells. FIG. 7A illustrates that FITC-BSA was also delivered with high efficiency into the cells. The results of these experiments demonstrated that our proposed method can effectively deliver large molecules (e.g., proteins) into cells. The scale bar represents 20 µm. Further investigation was conducted to ascertain the possibility of using delivery methodology to transfect plasmid DNAs into cells, given that the delivery of DNAs into cells is a key technique in studying cell biology. Two types of plasmids, GFP and mCherry, were delivered into the cells by the magnetic glass rod. FIGS. 8A and 8B show the plasmid expression of mCherry and GFP in the cells, respectively. The scale bar represents 40 µm.

With the delivery methodology described, there is provided a system and a method which allows a high-throughput and vector-free intracellular delivery of small cells using a magnetic glass rod. This invention addresses the critical need for high-throughput and high-efficiency methods for delivering various materials into cells. The technical advantages of this invention includes:

1) The methodology does not make use of bio-, chemical- or physical-agents as vehicles to deliver, for example, protein into cells. The advantage to do away the use of agents can ensure no contamination of the cells with undesired agents or side effects caused by such agents. Further, there is no issue of undesirable bonding of substance to be delivery and the agents, and thus there is no issue of complications caused by de-bonding of the substance after entering into the cells.
2) The methodology does not require a vector to deliver plasmids into cells.
3) The methodology can achieve results of delivery of substance in a matter of minutes. This is to compared with conventional method which could take hours.

This invention relates to the high-throughput delivery of exogenous macromolecules (DNAs, RNAs and proteins) into the cell. In particular, the invention relates to the use of a magnetic glass rod and a magnet to achieve high through-put intracellular delivery for adherent cells.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. It is also to be noted that certain features in connection with the invention are not explained in great detail for brevity reason. However, such features are readily understood by a skilled person in the art. For example, a skilled person would understand that the automation of the system can be achieved by linked different components in the systems. Also, a skilled person in the art will be aware of the prior art which is not explained in the above for brevity purpose.

The following references are incorporated in their entirety and a skilled person is considered to be aware of disclosure of these references.

REFERENCES

1. CATIONIC LIPIDS FOR INTRACELLULAR DELIVERY OF BIOLOGICALLY ACTIVE MOLECULES (U.S. Pat. No. 5,459,127 A; CA2079814A1; CA2079814C; DE69131347D1; DE69131347T2; EP0523189A1; EP0523189A4; EP0523189B1; U.S. Pat. No. 5,264,618; WO1991016024A1)
2. INTRACELLULAR DELIVERY OF MACROMOLECULES (U.S. Pat. No. 5,643,599 A; CA2223788A1; EP0831778A1; WO1996040060A1)
3. TAT-DERIVED TRANSPORT POLYPEPTIDES AND FUSION PROTEINS (U.S. Pat. No. 5,804,604 A)
4. METHODS AND PRODUCTS RELATED TO THE INTRACELLULAR DELIVERY OF POLYSACCHARIDES (US 20060083711 A1; WO2005110438A2; WO2005110438A3)
5. INTRACELLULAR DELIVERY (WO 2013059343 A1; CA2852672A1; CN103987836A; EP2768942A1; EP2768942A4; US20140287509)
6. INTRACELLULAR DELIVERY AND TRANSFECTION METHODS AND DEVICES (US 20140273229 A1)
7. SURFACE-MODIFIED NANOPARTICLES FOR INTRACELLULAR DELIVERY OF THERAPEUTIC AGENTS AND COMPOSITION FOR MAKING SAME (U.S. Pat. No. 8,865,216 B2; US20090136585; US20150139906; WO2009020865A1)
8. CELL PENETRATING PEPTIDES FOR INTRACELLULAR DELIVERY OF MOLECULES (WO 2014053622 A1; EP2951196A1; US20160089447; WO2014053879A1)
9. INTRACELLULAR DELIVERY OF BIOLOGICALLY ACTIVE SUBSTANCES BY MEANS OF SELF-ASSEMBLING LIPID COMPLEXES (WO 1991017424 A1)
10. NANOPARTICLE-AMPHIPOL COMPLEXES FOR NUCLEIC ACID INTRACELLULAR DELIVERY AND IMAGING (U.S. Pat. No. 8,063,131 B2; US20090322327)
11. RECOMBINANT PROTEIN FOR INTRACELLULAR DELIVERY OF SIRNA AND COMPOSITION COMPRISING THE SAME (U.S. Pat. No. 8,957,186 B2; US20130150287)
12. CATIONIC AMPHIPHILES FOR INTRACELLULAR DELIVERY OF THERAPEUTIC MOLECULES (U.S. Pat. No. 5,925,628 A; WO1998043994A1)
13. INTRACELLULAR DELIVERY OF SMALL MOLECULES, PROTEINS, AND NUCLEIC ACIDS (U.S. Pat. No. 7,420,031 B2; CA2516677A1; EP1601373A2; EP1601373A4; U.S. Pat. No. 7,166,692; US20040209797; US20060106197; US20090081791; WO2004078933A2; WO2004078933A3)
14. Kam, Nadine Wong Shi, Zhuang Liu, and Hongjie Dai. "Functionalization of carbon nanotubes via cleavable disulfide bonds for efficient intracellular delivery of siRNA and potent gene silencing." Journal of the American Chemical Society 127.36 (2005): 12492-12493
15. Derossi, Daniele, Gerard Chassaing, and Alain Prochiantz. "Trojan peptides: the penetrating system for intracellular delivery." Trends in cell biology 8.2 (1998): 84-87.
16. Gupta, Bhawna, Tatiana S. Levchenko, and Vladimir P. Torchilin. "Intracellular delivery of large molecules and small particles by cell-penetrating proteins and peptides." Advanced drug delivery reviews 57.4 (2005): 637-651.
17. R. C. Hogg, F. Bandelier, A. Benoit, R. Dosch, and D. Bertrand, "An automated system for intracellular and intranuclear injection," Journal of Neuroscience Methods, vol. 169, no. 1, pp. 65-75, 2008.
18. Kolhar, Poornima, Nishit Doshi, and Samir Mitragotri. "Polymer Nanoneedle-Mediated Intracellular Drug Delivery." Small 7.14 (2011): 2094-2100.

The invention claimed is:

1. A system of delivering particles of nano-scale into mammalian cells with a diameter of 50 µm or less, comprising a container containing the mammalian cells, the particles, a pressure-exerting member for generating transient apertures of substantially 1-200 nm on surface of the cells, a magnetic mechanism configured to generate a magnetic force to act on the pressure-exerting member thus to move the pressure exerting member, a control mechanism for effecting movement of the pressure-exerting member in a predetermined motion pattern, a balance configured to indicate magnitude of pressure exerted on the surface of the mammalian cells, and a monitoring mechanism, wherein:
the pressure-exerting member has a length not longer than one-third of the width of the container;
the pressure-exerting member and the particles are free of chemical bonding there between before a delivery exercise;
the pressure-exerting member has a cylindrical profile, with an outer shell containing an iron core and a biocompatible material for securing the iron core in the outer shell;
the outer shell is made of an inert material or glass, and the biocompatible material is polydimethylsiloxane; and
the system is free of use of electrical field in the delivery of the particles.

2. The system as claimed in claim 1, wherein the container is in the form of a Petri dish.

3. The system as claimed in claim 2, wherein the Petri dish has a diameter of substantially 35 mm, the pressure-exerting member has a length of substantially 1 cm and inner and outer diameters of substantially 0.7 mm and 1 mm, respectively, and the iron core has a length of substantially 0.75 cm.

4. The system as claimed in claim 1, wherein the outer shell is open-ended to expose the iron core.

5. The system as claimed in claim 4, wherein the magnetic mechanism includes i) a magnet situated below the first stage and ii) a second stage supporting the magnet, the second stage is configured to be movable linearly, whereby movement of the second stage produces corresponding movement of the magnet.

6. The system as claimed in claim 5, comprising the balance on which the second stage situates, the balance for detecting and indicating magnetic force generated on the pressure-exerting member in the container.

7. The system as claimed in claim 1, comprising a first stage for supporting the container, the first stage is configured to be movable vertically and linearly for adjusting the position of the container.

8. The system as claimed in claim 7, wherein the monitoring mechanism include a camera situated above the first stage for monitoring movement of the pressure-exerting member in use.

9. The system as claimed in claim 8, comprising a computer system for coordinating movement of the magnet and thus the magnetic force generated on the pressure exerting member, controlling horizontal position of the second stage, controlling horizontal position and vertical position of the first stage, and movement of the pressure-exerting member in the container during a particle delivering exercise.

* * * * *